United States Patent [19]

Schuellein

[11] Patent Number: 5,342,290
[45] Date of Patent: Aug. 30, 1994

[54] APPLIANCE FOR IMPROVED RADIOGRAPHIC VISUALIZATION OF THE CERVICAL SPINE

[76] Inventor: Stephen C. Schuellein, 6904 Manatee Ave. West Apt. 14A, Bradenton, Fla. 34209

[21] Appl. No.: 42,280

[22] Filed: Apr. 2, 1993

[51] Int. Cl.$^5$ .............................................. A61H 1/02
[52] U.S. Cl. ....................................... 602/36; 602/35; 128/870; 5/623; 5/625; 5/628
[58] Field of Search ................ 128/845, 870; 602/35, 602/36; 5/601, 621, 622, 623, 625, 628; 378/208, 209

[56] References Cited

U.S. PATENT DOCUMENTS

| | | | |
|---|---|---|---|
| 3,512,189 | 5/1970 | Swanson | 128/845 |
| 3,629,581 | 12/1971 | Smith | 5/621 |
| 4,166,459 | 9/1979 | Nightingale | 602/35 |
| 4,177,807 | 12/1979 | Ocel et al. | 128/845 |
| 4,383,524 | 5/1983 | Boger | 602/36 |
| 4,669,106 | 5/1987 | Ammerman | 5/601 |
| 4,674,483 | 6/1987 | Frederick | 5/628 |
| 5,201,089 | 4/1993 | Ferreira | 118/870 |
| 5,213,062 | 5/1993 | Canady, Jr. | 128/870 |

*Primary Examiner*—Richard J. Apley
*Assistant Examiner*—Jeanne M. Mollo
*Attorney, Agent, or Firm*—William J. Daniel

[57] ABSTRACT

The X-ray exposure in lateral projection of the cervical spine region of a traumatized patient resting on a trauma board or like emergency carrier is facilitated by an appliance in the form of a traction board having a flat base plate adapted to fit in telescoping relation slidingly beneath an end portion of the trauma board and an integral upstanding traction plate projecting upwardly from the base plate for abutting contact with the end edge of the trauma board or other carrier. The traction board is equipped with e.g. a belt or a C-shaped channel for engaging the same to an overlying portion of the trauma board. Laterally spaced apart guide apertures are provided adjacent the side edges of the traction plate for passage of the free ends of traction straps gripping with wrist loops at their opposite ends the wrists of the patient and the free ends are adapted to be affixed and held to the outer face of the traction plate, preferably by so-called hook-and-loop fastening means, after tractive force has been applied thereto by an attendent to displace the shoulders of the patient to a sloping position clear of the exposure. The traction straps are preferably flat and the guide apertures are elongated in a direction perpendicular to the base plate and the free strap ends are preferably affixed to the face of the traction plate in juxtaposed relation generally parallel to the base plate.

7 Claims, 2 Drawing Sheets

APPLIANCE FOR IMPROVED RADIOGRAPHIC VISUALIZATION OF THE CERVICAL SPINE

BACKGROUND OF THE INVENTION

In the event of traumatic injury, e.g. in an automobile accident, a major fall or the like, the injured individual must be given immediate medical treatment and for this purpose, hospitals or similar institutions have established emergency rooms, trauma centers, or other immediate care facilities. For transportation from the scene of the accident to such facility, it is now routine practice for the patient to be arranged at the scene on what is known as a trauma or spine board. These boards are flat or planar for easy storage in a minimum of space, of generally rectangular shape with a length of seven feet or so, and are provided with handholes at spaced intervals along their side margins for carrying. A shortened version, intended mainly for torso support only, is illustrated in U.S. Pat. No. 4,127,120. Currently available trauma boards are equipped with restraining devices such as adjustable chest or torso straps, which usually criss-cross over the patient's chest or torso, being connected to the boards at the four opposite corners of the torso, and head immobilizer blocks to prevent as much as possible any movement of the head and neck by the patient and thus minimize the possibility of aggravation of any existing injuries. In addition, a cervical collar is usually placed on the patient for direct cervical support for the same reason.

Because of the likelihood of damage to the cervical spine due to whiplash and similar impact reaction, the trauma patient upon arrival at the trauma treatment facility is naturally under suspicion of cervical spine injury and one of the first concerns of the attending personnel, after administering immediate life-saving treatment, is to investigate whether such injury is in fact present. This requires the exposure by lateral projection, i.e. from a position to one side of the cervical region of the patient, of an X-ray or other radiographic photograph of the complete cervical section of the spine, including all seven bones of that region. This exposure must take place while the patient remains fully immobilized on the trauma board with a minimum of physical disturbance of the relative position on the board.

As is well recognized in the art, for example, U.S. Pat. Nos. 3,629,581, 4,383,524, 4,669,106, and 4,674,483, diagnostic radiography by lateral projection of the full cervical spine on a supine patient is troublesome. The natural position of the shoulders of a patient in that position is in lateral alignment with the sixth and seventh vertebrae of the cervical region which obstructs a clear view of those vertebrae. Prior attempts to overcome this problem have not proved entirely satisfactory from the standpoint of the trauma professional.

The traditional technique, that is still frequently employed today, is for an attendant to stand at the foot of the patient anchored on the trauma board resting on a gurney cart facing toward the patient's head, bend from the waist as necessary to grasp a hand or wrist of the patient in each hand, and pull firmly toward the feet until the shoulder girdle is displaced angularly out of lateral coincidence with the sixth and seventh vertebrae. However, it is difficult for the attendant in this bent-over position to judge the correct degree of the force to be applied to the patient's arms with the risk that such force is either insufficient or in excess of what is needed. Moreover, the attendant is at risk of exposure to stray X-ray radiation since effective shielding under the circumstances is virtually impossible.

One early visualization appliance disclosed in U.S. Pat. No. 3,629,581 sought to avoid this problem by resort to mechanical advantage in the form of a double-acting windlass mounted on the outer face of the footboard against the opposite face of which the feet of the patient are pressed. Wrist straps having an adjustable loop at one end for engaging the patient's wrists are connected at their other end to the windlass. Rotation of the handle of the windlass winds the straps equally, drawing the patient's arms and shoulder girdle footwardly. Reverse rotation is prevented by a pawl engaging teeth on a pinion rotating with the windlass until the pawl is released.

But the mechanical advantage can prove to be a disadvantage because it precludes any direct sense by the operator of the magnitude of the applied force and introduces the possibility of excessive traction being applied with consequential injury. Moreover, satisfactory operation of this arrangement is necessarily dependent upon a state of rigidity for the patient's legs to resist the applied tractive force. Unless the patient is conscious and cooperative, which is often not the case, or the legs are restrained by straps or by pressure exerted manually by the attendant, the knees will tend to flex when subjected to significant axial compressive force and defeat the desired result. Finally, this approach is absolutely contra-indicated where there is injury to the leg and pelvic region, as can easily be present in trauma patients.

A generally similar but simplified suggestion appears in U.S. Pat. No. 4,383,524 using an inextensible strap which is attached to the wrists by wrist bands at its ends, or, alternatively, directly to the shoulders via shoulder slings, and passed as a U-shaped loop of adjustable length beneath the patient's feet. Separate straps for each wrist can be used instead of a single strap with the free ends being joined together beneath the feet by hook-and-loop fasteners, such as are sold under the tradename "VELCRO". Initially, after the wrist bands are in place, the patient's knees are flexed slightly while the U-shaped loop of the strap is pulled tight against the patient's feet. Then the knees are straightened so as to tension the U-shaped loop and apply traction to the arms and thence to the shoulders and thereby retract the shoulders in a distal direction clear of the lower cervical spine.

Obviously, the degree to which the knees are flexed at the beginning determines the degree of shoulder retraction and gauging the correct degree is more often than not a matter of trial and error which is awkward and time-consuming. Nor can one effectively circumvent this problem by deliberately selecting too much flexure with the expectation that the patient can compensate by maintaining the legs in a suitable intermediate position. But without the knees being locked in straight position, it is difficult for the patient to exert in stable fashion the considerable amount of force required for sufficient shoulder retraction. At the other extreme, too little flexure results immediately in inadequate retraction.

As with the earlier system, the intervention of the legs in maintaining tractive tension requires a conscious and cooperative patient or the assistance of an attendant and in any case disqualifies patients with injuries to their lower extremities.

Another system utilizing mechanical advantage but in a far more complicated arrangement is found in U.S. Pat. No. 4,669,106 wherein mechanical pressure is applied directly against the tops of the shoulders in a footward direction while bodily movement in the same direction is prevented. To this end, shoulder-contacting abutments are mounted adjustably on a pressure plate slidably supported at the upper end of a trauma board and a mechanical winch is operated to mechanically drive the plate distally and thus apply sufficient pressure via the abutments directly against the shoulder surfaces to cause their retraction. To keep the body from sliding axially under this pressure, a pontel-like post is fixed to an adjustable median point of the board for engagement by the crotch or perineal region of the patient.

Both the abutment-carrying pressure plate and the crotch pontel must be already in position on the board in advance of placement of the patient thereon so that every trauma board would require rather expensive modification for the practice of this invention. Also, given the significant level of traction force required for shoulder retraction, the application to the crotch region of resistance sufficient to withstand such force would be uncomfortable if not downright painful and would be totally unacceptable if injuries to the pelvic region e.g. a pelvic fracture, were present. Finally, if, as is usual, a cervical collar has been affixed to the patient, it would interfere with the proper positioning of the abutments against the tops of the shoulders.

A shoulder retraction appliance specifically configured for cooperation with computerized axial tomography (CAT) scanning units is shown in U.S. Pat. No. 4,674,483. Such units have a channel-like axial recess in which the patient rests and the appliance consists of a concavely curved baseboard resting within the recess and supporting an upstanding footboard buttressed from below to form a rigid assembly extending partially beneath the patient's legs with the feet planted against the footboard. A shoulder sling encircles each shoulder and is connected to a tether which extends to the footboard and is anchored after sufficient tensioning to the top of the latter by a wedge-type cleat.

In practice, shoulder slings perform poorly because of the difficulty in preventing such slings from slipping free of the shoulders, particularly since movement of the shoulders under traction to a distally retracted position increases the slope angle of the shoulders from the neck to the axilla. This inherently promotes sliding disengagement of the slings which naturally follow the path of least resistance. Further, if a cervical collar and/or head restraining blocks are in position, attachment of shoulder slings becomes almost impossible unless the straps and blocks are first removed, making possible movement of the patient, who may not be in a mentally competent state at the time, and increasing the danger of cervical complications.

The use of a curved baseboard while ideal for CAT scan units is undesirable for association with present day trauma boards which are flat for storage in the cramped quarters of an EMS vehicle since the curved baseboard will be unstable and subject to rocking movement if placed either on or below an end of a trauma board. Likewise, wedge-type cleats for gripping the free ends of the shoulder sling tethers permit release of the tether ends only when additional tension is applied to the tethers. If the operative tension for satisfactory shoulder retraction has already approached the maximum desirable level, this added tension for release of the tethers could have adverse effects on the nerves, muscles, and joints of the shoulders of the patient.

Although visualization of all seven of the cervical vertebrae in a single X-ray radiograph is ideal for diagnostic purposes, this is not always possible. There are physical conditions which preclude this ideal result even under the best of circumstances and equipment, such as patients with a seventh cervical rib or with such developed shoulder muscularity that maximum retraction fails to eliminate the obstruction of the seventh cervical vertebrae in lateral projection. For these special cases, a variation known as the "swimmer's" or Twining position has been developed. To achieve this position, one shoulder is retracted distally while the opposite arm is raised above the head with the elbow bent at right angles and the forearm is adducted over the head. With the patient in this position, an X-ray beam is able to pass through an area centered on the seventh cervical vertebrae free of superimposition of the shoulders. The resultant image while inferior diagnostically to a true lateral radiograph of the full cervical spine, is sufficient useful to rule out, or identify, as the case may be, a fracture, dislocation, or subluxation of the sixth and seventh cervical vertebrae. It is critical to the successful resort to this variant position that one is able to raise one shoulder while elevating the other to an extent permitting visualization of the area of interest.

Visualization appliances that cannot accommodate the "swimmer's" or Twining position, such as U.S. Pat. No. 4,669,106, have limited utility and are less desirable to a "full-service" trauma facility.

There is thus a need in the field of trauma medicine for an appliance for assisting the radiographic visualization in lateral projection of the complete cervical spine that is free of the various disadvantages and drawbacks of the devices that have so far been proposed for this purpose.

OBJECTS OF THE INVENTION

The object of the invention is to provide an appliance of the type in question which is simple and inexpensive to manufacture, is virtually fool-proof to use in a minimum of time, accommodates easily with standard trauma boards, does not require that the patient be removed from or adjusted in position on the trauma board, is not hampered by the presence of restraint adjuncts, such as cervical collars or head blocks, is not dependent on leg rigidity for successful operation but takes advantage of the natural rigidity of the trauma board, does not require the continued presence of an attendant after initial adjustment so that the attendant need not be exposed to any radiation, is as suitable for patients in a comatose condition as for conscious and cooperative ones, entails a minimum risk of added or new injury to the patient even where injury to the lower extremities is present, and is adapted where necessary for radiographic exposure of patients in the "swimmers" or Twining position.

DETAILED DESCRIPTION OF THE INVENTION

Figure 1:
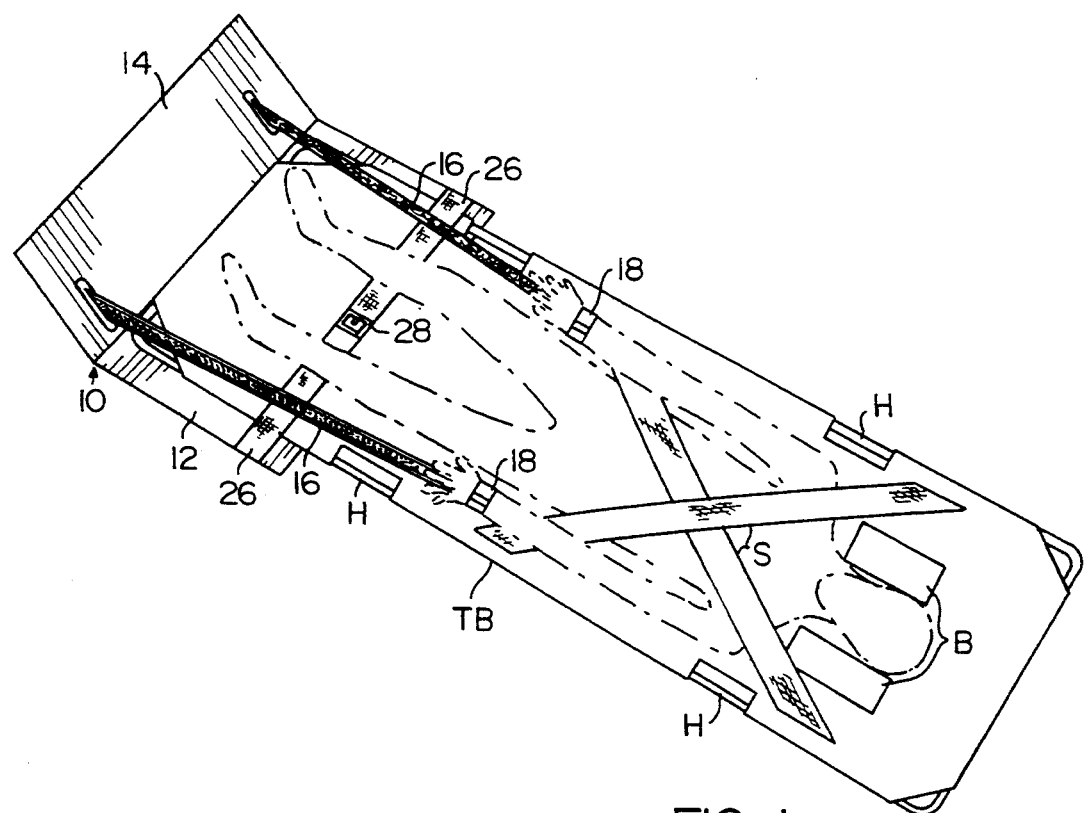
FIG. 1 is a perspective or isometric view showing the patient in dot-dash lines lying on a trauma board with the appliance of the invention in operative position in association with the trauma board.

The basic element of the appliance of the invention is a traction board generally designated 10 by means of which tension or traction force can be applied to traction straps stretching to the patient's wrists. The traction board consists mainly of a base plate 12 that is adapted to fit snugly beneath an end of any standard trauma board designated TB in direct, face-to-face contact with the flat undersurface of the trauma board and an integral upstanding traction plate 14 to which the tensioned straps can be anchored or attached and held in tensioned condition.

As a rule, trauma boards are made with one end equipped with one or more sets of laterally spaced openings (not visible in the drawings) to receive neck and head supporting blocks B for contraining the neck and head of the patient and which serve as the head. In that case, the base plate 12 of the tension board 10 of the invention is intended to fit under the opposite or foot end. For trauma boards that are symmetrical in design, the base plate should be capable of fitting under either end. In any case, the base plate should be flat or planar in nature, as distinguished from concavely curved or dish-shaped, in order to cooperate with the flat undersurface of the trauma board or, alternatively, to slide unobtrusively beneath one end of a thin mattress carried on an emergency stretcher (not shown) without substantial displacement of the mattress end from its normal condition. The trauma board TB, emergency stretcher and similar patient supports are herein referred to collectively as "portable carriers".

Trauma boards also typically are provided as shown with a plurality of axially spaced handholes H along their opposite side margins and shoulder straps S adapted to be arranged in criss-crossing relation across the chest region of the patient to secure the patient to the trauma board for transportation. These features are conventional and form no part of the invention.

The base plate should be rigid and can be constructed of a flat piece of wood, plastic or even light-weight metal, such as aluminum, and should be relatively thin in thickness for the reason given above consistent with substantial rigidity for the particular material employed. It can be generally rectilinear in configuration when viewed in tap plan, as shown in the drawings or it can be tapered somewhat along its sides (not shown) and in either case, one end, which will be the leading end projecting beneath the trauma board or mattress, e.g. the narrower end for a tapered shape, can be rounded, if desired. In length, it should overlap, i.e. telescope in operative position, with a lengthwise portion of the trauma board TB or mattress sufficient to minimize any danger of the base plate tilting or rocking about a transverse axis relative to the trauma board, say at least about one foot and preferably somewhat longer up to two feet or so. In width, it can vary up to the approximate lateral dimension of an average large-sized patient, say about 24–30 inches, or even greater if desired, extending on either side of the trauma board, as shown, although the added width gives no particular advantage and may make the unit more cumbersome to handle, but it can also be considerably narrower, down to perhaps about 7–12 inches, provided the width is sufficient for structural strength and rigidity and firm stable anchorage beneath the trauma board without risk of tilting or rocking about a longitudinal axis.

Upstanding from one end of the base plate 12, which in the case of a tapered base board would be the larger end, and integral therewith, via a rigid connection, dependent largely on the choice of the material of construction, is the traction plate 14 which again is constructed from any suitable rigid material, such as wood, plastic or light-weight metal. It can where appropriate for the material in question be made integral with the base board, e.g. by molding or shaping, or be formed separate from the base plate and fastened thereto by suitable connectors, such as bolts, screws, rivets or the like dependent largely on the choice of the material of construction.

The traction plate 14 is preferably flat but could be slighted curved about a central vertical axis, i.e. perpendicular to the plane of the base plate, which would require a corresponding shaping of the end of the base board, a complication in the manufacture of the latter having no notable benefit. It is preferably perpendicular to the base board to define a square corner with the latter for abutment with the usual square end of the trauma board TB or stretcher mattress but slight deviation from the perpendicular would not be seriously objectionable.

A pair of traction straps 16 adapted to be secured around the wrists of the trauma patient are provided and are formed of substantially inextensible material, such as a heavy fabric tape braided or woven from threads or filaments of natural fibers or synthetic polymers or thick solid ribbons of such polymers having the necessary properties. Generally, synthetic polymers are preferable from the standpoint of maintaining aseptic conditions. The traction straps are of sufficient length to extend from the wrists of tall patients to the traction plate with enough excess for attachment to that plate, or around four feet.

Securely attached to one end of each strap in more or less orthogonal relation, e.g. by such means as rivets or heavy stitching (not shown), is a wrist band 18 of sufficient length to wrap comfortably around the wrists of a large sized patient and overlap a reasonable amount at its ends. The overlapping end portions of bands 18 are adapted to be secured together and for this purpose cooperating strips of so-called hook-and-loop fastening material, such as is sold under the tradename "VELCRO", are preferably affixed to opposite surfaces of such end portions, i.e., the hook-carrying strip being arranged on one surface of one end portion and the loop-carrying strip being arranged on the opposite surface of the opposite end portion. The fastening material is not indicated in the drawings since it is arranged in substantially the same manner as in U.S. Pat. No. 4,383,524 described above. By adjusting the extent of overlap of the end portions during fastening, the size of the loop created when the end portions of the wrist strap are secured together can be easily varied to fit the wrists of individual patients.

Other ways of joining the ends of the wrist bands for forming the adjustable wrist loops can be substituted, e.g. buckles or the like, if preferred.

The free ends 20 of the traction straps, i.e. the ends opposite to the wrist bands, are intended to be anchored to the traction plates after being subjected to sufficient tension to transmit the necessary traction force to the wrists of the patient and thence to the shoulders, For this purpose, elongated or oblong guide openings or slots 22 are formed in the traction plate for passage of the straps therethrough at a convenient relatively short distance from the side edges of the traction plate and intermediate the upper and lower edges of the traction plate so that the two guide openings are situated generally symmetrically of the central vertical axis of the plate with a separation between them roughly equal to the natural separation between the wrists of an average patient when the wrists are extended comfortably along the sides of the patient's torso, say 20-24 inches or so.

The long axis of the guide openings preferably extends vertically, i.e. perpendicular to the plane of the base boards. The lesser dimension of these guide openings is chosen according to the thickness of the traction straps, but is sufficiently larger to enable the free ends of the straps to be freely inserted through the guide openings speedily and without jamming. The greater (preferably vertical) dimension is desirably made somewhat larger than the width of the straps, even double or so, in order that the straps can shift slightly in the openings and facilitate their anchorage in juxtaposed relation, as is prefered, on the end face of the traction board.

The vertical height of the openings above the plane of the base board can vary depending on the height of the traction plate but should be significant so as to create a leverage when a tensioned traction strap is present therein urging the base plate downwardly against whatever underlying surface the trauma board is resting on and a height of about six to eight inches more or less will usually suffice. If desired, additional sets of guide openings (not shown) can be provided at different heights, allowing the most advantageous height for a specific patient to be selected.

According to the construction material of the traction plate, and particularly in the case of wood, the permanent insertion into each guide opening of a grommet (not shown separately) or the like having rounded end surfaces may be advisable to minimize abrasion and friction between the edge of the guide openings and the straps and promote easy, fast insertion of the straps ends therethrough.

The free ends of the tensioned traction straps are anchored or attached to the surface of the traction plate 14 facing away from the patient and in order to achieve a rapid and reliable attachment of the free ends of the straps, use is again made of cooperating hook-and-loop fastening material. Thus, a block-like strip 24 of one such material, e.g. the hooked section, is attached, e.g. by adhesive, to the face of the traction plate for each of the traction straps in a convenient position intermediate the two spaced apart guide openings in the boards while a strip of the other cooperating material, e.g. the looped section, is secured, e.g. by stitching, to one side of an end portion of each of the traction straps. The strips for the respective traction straps can, of course, be combined as shown into a common oversize strip having vertically adjacent regions for the two straps to be engaged thereto in side-by-side oppositely extending relation.

It is imaginable that the guide openings could be arranged with their long axes extending parallel to the plane of the base boards, i.e. horizontally, with the strip of anchoring material, i.e. the hooked or looped strip, disposed vertically above or below each of the openings. In that case, a common anchoring strip would not be feasible. It is also possible that the traction straps could be oval or circular in cross-section rather than flat but these alternative shapes are less well adapted for the use of hook-and-loop fastening material. For such shapes of straps as well as for the flat straps themselves, a different type of fastening means could be substituted, e.g. a "scissors" type of clamp somewhat similar to a clamp forceps, but with some loss in ease of manipulation.

Figure 2:
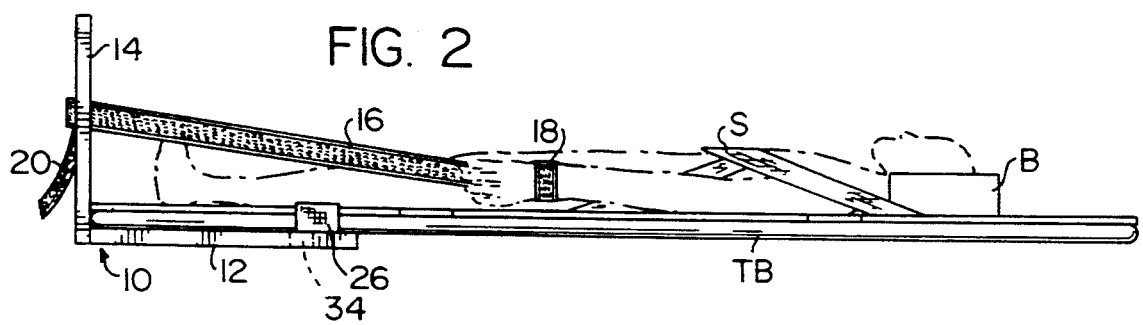
FIG. 2 is a view similar to FIG. 1 but taken in side elevation.
Figure 3:
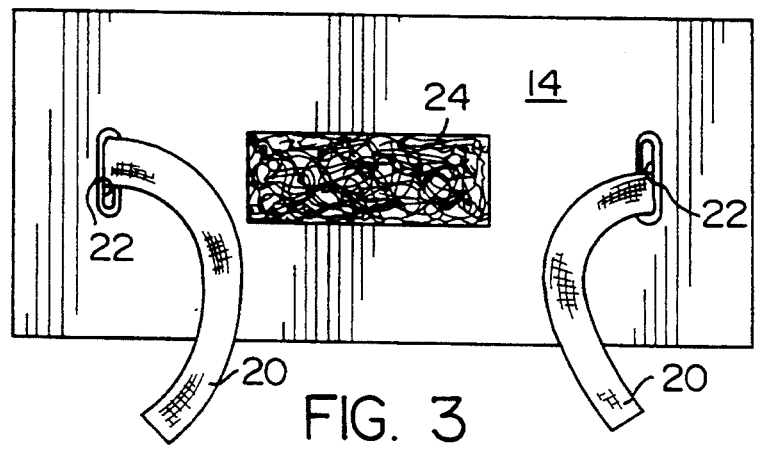
FIG. 3 is an end view of the appliance looking in the direction of the patient's head showing the ends of the tension straps in an intermediate position prior to being attached or anchored to the foot plate.
Figure 4:
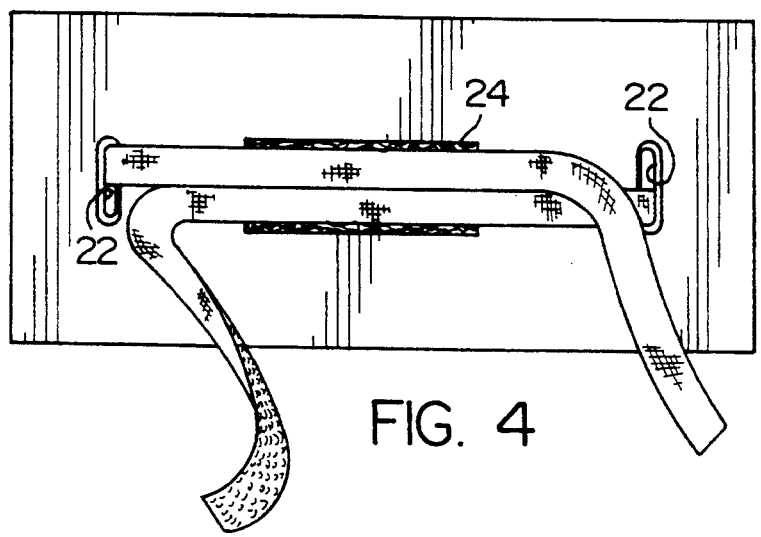
FIG. 4 is an end view similar to FIG. 3 but showing the ends of the tension straps in their final operative position anchored to the foot plate.
Figure 5:
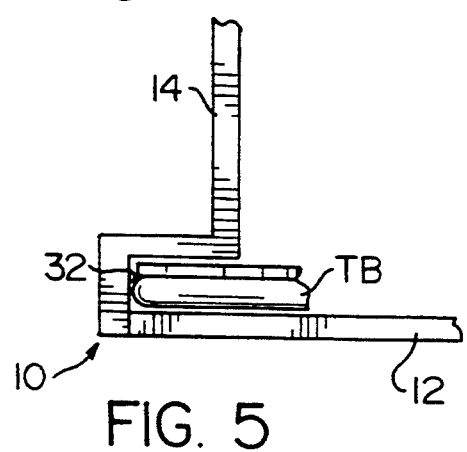
FIG. 5 is a modification showing an alternative arrangement for engaging the appliance of the invention in operative relation to the trauma board

It is an advantagious feature to provide the base plate with some means cooperating with the trauma board for engaging the base plate more securely in operative relation to the trauma board. In the embodiment of FIGS. 1 and 2, this means takes the form of lengths of a flat security belt 26 each affixed at one end thereof to the opposite side margins of the base plate a short distance from the inner edge of the base plate, i.e. in the direction of the patient's head, with the other ends thereof being adapted to be passed over the overlying portion of the trauma board and fastened together, e.g. with a buckle 28 or hook-and-loop fastening means as described above.

It is usually desired that the security belt pass beneath the legs of the patient but if the need should arise, it can be passed and fastened over the patient's legs and thus maintain those legs in a straightened condition.

In an alternative embodiment, the lower end of the traction plate proximate to the base plate is offset and forms with the remote end margin (relative to the patient's head) of the base plate a C-shaped channel 32 into which the end margin of the trauma board TB can be inserted and held. In another alternative, not shown, releasable clamps could be mounted on the side edges of the base plate for clamping engagaement with the overlying side edges of the trauma board and other equivalents could be devised.

To facilitate storage of the appliance, the base plate 12 can have a central opening 34 therein, indicated in dotted lines in FIG. 2, by which it can be suspended from a hook for out-of-the-way storage in the trauma facility. As a similar convenience, the traction straps 16 could be stored in a pouch (not shown) having a hanging loop for hanging on the same hook or a belt loop for penetration by the belt 26 or a hook-and-loop fastening strip for attachment to the attachment strip 24.

The use of the appliance of the invention will be obvious from its description set forth above, as will be the fact that the straps can be used singly instead of both together, e.g. for patients in the Twining position. In use, the wrist bands of the traction straps are engaged to one or both of the patient's wrists either before or after threading of the free ends of the straps through the guide openings. The medical attendant grasps the free ends of the straps projecting beyond the guide openings one by one in turn and then applies a lengthwise traction force to the strap end by pulling the same.

It has been found that by standing erect at the end of the trauma board or stretcher supporting the patient and pulling carefully on the end of a strap with both hands, or if one is sufficiently strong, with one hand while bracing with the other against the top edge of the traction plate, sufficient tractive force can easily be applied to achieve in most cases satisfactory retraction of the shoulder girdle of the patient for visualization in lateral projection of the cervical spine region. Because the base plate is wedged between the trauma board or stretcher mattress and the underlying gurney or stretcher, with the traction plate in direct abutting contact against the end edge of the trauma board or mattress, the traction plate is able to maintain substantial tractive force on the traction straps and thence on the patient's arms and shoulders once that force has been applied by the attendant. It is not required that the feet of the patient be braced against, or even be in contact with, the traction plate inasmuch as the torso or shoulder straps associated with the trauma board or even the weight of the patient on the yielding mattress offers enough resistance to prevent the patient from sliding toward the traction plate. Hence, the legs of the patient need not be involved in any way in the procedure as is important where injuries to the extremities are present.

On rare occasions, a patient may be brought to the emergency facility without being placed on a trauma board. When such a patient is under "C-spine precautions", i.e. suspicion of cervical spine injury, according to accepted procedure, the head and neck are immobilized while the patient is resting on a stretcher and a lateral cervical spine exposure is made. Where a mattress is present on the stretcher, the appliance of the invention can be utilized as described above. But if there is no mattress, the present appliance is nevertheless of value in facilitating the exposure when placed directly beneath the leg extremities. The weight of the leg extremities, augmented if need be with the straps 26 passing around the legs, combined with the pressure urging the base board against whatever its supporting surface may be, due to the action of the traction force working through the leverage of the vertical position of the guide opening in the traction plate above the base plate is ordinarily sufficient to hold the appliance in operative position without the feet of the patient coming in contact with the traction plate.

In the course of the above detailed description, a number of altervatives or variations have been identified and others may well occur to the skilled worker in the field without departing from the spirit of the invention.

I claim:

1. An appliance for facilitating the visualization in lateral projection for radiographic exposure of the complete cervical spine region of a traumatized patient resting on an elongated portable carrier, which comprises a traction board comprising a planar generally rigid base plate adapted to fit in operative relation beneath an overlying distal end portion of the portable carrier with the pedal extremities of such patient in superposed relation thereto, a traction plate rigidly fixed along a lower edge thereof to an end edge of said base plate in upstanding relation to said base plate, said traction plate projection generally perpendicularly above the base plate to terminate in an upper edge spaced from the plane of said base plate for generally abutting contact with an end of the portable carrier, said traction plate having a guide opening therein situated adjacent each of two opposite side edges thereof intermediate its lower and upper edges thereof, and means on said traction board for engaging an overlying portion of the portable carrier to maintain the same in operative relation; a pair of flexible substantially non-extensible traction straps each adapted to pass freely through one of said guide openings in said traction plate, each such strap having at an end thereof remote from said traction late and adjustable loop for engaging a wrist of the patient; and strap attachment means for each of said traction straps for anchoring to the face of said traction board remote from the patient the end of each of said traction straps opposite the wrist loop, said attachment means comprising cooperating hook-and-loop fastening strips, one of which is mounted on said remote face of said traction plate in general alignment with the corresponding guide opening and the other is carried on the opposite end of the traction strap, whereby with the wrist loop of each said traction strap engaging a wrist of the patient and the opposite end of said strap passed through the guide opening in said traction plate on the same side as the wrist engaged thereby, traction force can be applied individually to the straps sufficient to retract the patient's shoulders toward the patient's feet out of lateral coincidence with the cervical spine region, and the opposite ends of said straps can be separately anchored by the fastening strips therefor to said remote traction plate face to maintain the applied traction force and the retraction of the patient's shoulders while the cervical spine region is radiographically exposed.

2. The appliance of claim 1 wherein the fastening strips on said remote face of the traction plate for anchoring the opposite ends of said two traction straps are constituted by separate regions of a common fastening strip mounted on said remote face.

3. The appliance of claim 1 wherein said wrist loop comprises a wrist strap affixed to the remote end of each traction strap in orthogonal relation thereto and cooperating hook and loop fastening strip are disposed on portions of said wrist strap adjacent its opposite ends to join such ends in overlapping relation and form said wrist strap into a loop.

4. The appliance of claim 3 wherein said cooperating hook and loop fastening means on the portions of said wrist strap are disposed on opposite surfaces of said portions.

5. The appliance of claim 1 wherein said base plate and traction plate each have a dimension transverse to the length of the portable carrier that is adapted to be at least approximately equal to the distance between the shoulders of a patient of average size.

6. The appliance of claim 1 wherein said traction straps are formed as flat tapes and said guide openings adjacent the opposite sides of said traction plate are slots extending generally perpendicularly of the plane of said base board.

7. The appliance of claim 6 wherein the fastening strips for said traction straps form part of a common strip for both straps and said common strip is mounted on said remote face of said traction plate intermediate said slots, the ends of the traction straps being anchored to the common strip in generally juxtaposed relation.

* * * * *

UNITED STATES PATENT AND TRADEMARK OFFICE
CERTIFICATE OF CORRECTION

PATENT NO.   : 5,342,290
DATED        : August 30, 1994
INVENTOR(S)  : STEPHEN C. SCHUELLEIN It is certified that error appears in the above-identified patent and that said Letters Patent is hereby corrected as shown below:

Col. 9, line 58, Change "projection" to --projecting--.

Col. 10, line 7, change "late and" to --plate an--.

Signed and Sealed this

Twenty-fifth Day of October, 1994

Attest:

BRUCE LEHMAN

*Attesting Officer*   *Commissioner of Patents and Trademarks*